US010281424B2

(12) United States Patent
Fomina et al.

(10) Patent No.: US 10,281,424 B2
(45) Date of Patent: May 7, 2019

(54) ELECTRODE ARRANGEMENT WITH IMPROVED ELECTRON TRANSFER RATES FOR REDOX OF MOLECULES

(71) Applicant: Robert Bosch LLC, Broadview, IL (US)

(72) Inventors: Nadezda Fomina, Fremont, CA (US); Autumn Maruniak, Fremont, CA (US); Christopher Johnson, Mountain View, CA (US); Habib Ahmad, Sunnyvale, CA (US); Sam Kavusi, Menlo Park, CA (US)

(73) Assignee: Robert Bosch GmbH, Stuttgart (DE)

( * ) Notice: Subject to any disclaimer, the term of this patent is extended or adjusted under 35 U.S.C. 154(b) by 201 days.

(21) Appl. No.: 15/194,290

(22) Filed: Jun. 27, 2016

(65) Prior Publication Data

US 2017/0370870 A1    Dec. 28, 2017

(51) Int. Cl.
| | | |
|---|---|---|
| *G01N 27/327* | (2006.01) | |
| *G01N 27/30* | (2006.01) | |
| *C25D 9/08* | (2006.01) | |
| *C25D 7/00* | (2006.01) | |
| *C25D 3/48* | (2006.01) | |
| *B05D 1/00* | (2006.01) | |
| *C12Q 1/00* | (2006.01) | |

(52) U.S. Cl.
CPC .............. *G01N 27/307* (2013.01); *B05D 1/60* (2013.01); *C12Q 1/004* (2013.01); *C25D 3/48* (2013.01); *C25D 7/00* (2013.01); *C25D 9/08* (2013.01); *G01N 27/305* (2013.01); *G01N 27/327* (2013.01); *G01N 27/3277* (2013.01)

(58) Field of Classification Search
CPC .. G01N 27/327–27/3272; G01N 27/30; G01N 27/307

See application file for complete search history.

(56) References Cited

U.S. PATENT DOCUMENTS

| | | |
|---|---|---|
| 4,879,243 A | 11/1989 | Mura et al. |
| 4,968,400 A | 11/1990 | Shimomura et al. |
| 6,197,881 B1 | 3/2001 | Cosnier |
| 7,384,749 B2 | 6/2008 | Kayyem et al. |
| 7,544,438 B2 | 6/2009 | Nishizawa et al. |
| 2003/0148169 A1 | 8/2003 | Willner et al. |

(Continued)

FOREIGN PATENT DOCUMENTS

| | | |
|---|---|---|
| EP | 0187719 | 7/1986 |
| EP | 0368209 A1 | 5/1990 |

(Continued)

OTHER PUBLICATIONS

Malhotra et al., "Conducting polymer based on bimolecular electronic devices," PRAMANA—journal of physics, vol. 61, No. 2, Aug. 2003, pp. 331-343 (Year: 2003).*

(Continued)

*Primary Examiner* — Alexander S Noguerola
(74) *Attorney, Agent, or Firm* — Gerard Messina

(57) ABSTRACT

A coated electrode includes an electrode, a coating configured to immobilize biomolecules, and a coating configured to improve electron transfer rate. Methods of making the coated electrode are also provided. A biosensor comprises a plurality of electrodes, each electrode including the coated electrode.

43 Claims, 4 Drawing Sheets

(56) References Cited

U.S. PATENT DOCUMENTS

| | | | |
|---|---|---|---|
| 2006/0113187 A1 | 6/2006 | Deng et al. | |
| 2006/0115857 A1 | 6/2006 | Keen | |
| 2006/0269826 A1 | 11/2006 | Katz | |
| 2014/0274760 A1 | 9/2014 | Fomina et al. | |
| 2015/0241376 A1* | 8/2015 | Wang | G01N 27/3272 204/403.01 |
| 2015/0316499 A1 | 11/2015 | Jacks | |

FOREIGN PATENT DOCUMENTS

| | | |
|---|---|---|
| WO | 2006057722 | 6/2006 |
| WO | 2016019381 A1 | 2/2016 |
| WO | 2017013495 A2 | 1/2017 |

OTHER PUBLICATIONS

Sigma-Aldrich online catalog entry for poly-(3-decylthiophene-2,5-diyl) (Year: 2018).*

Bolat et al, "Fabrication of a Polyaniline Ultramicroelectrode via a Self Assembled Monolayer Modified Gold Electrode," Sensors 2013, 13, 8079-8094 (Year: 2013).*

Cooper et al., "Catalytic Reduction of Benzoquinone at Polyaniline and Polyaniline/Enzyme Films," Electroanalysis, 5(1993) 385-397 (Year: 1993).*

Chen et al., "Electrogeneration of Polypyrrole/Alginate Films for Immobilization of Glucose Oxidase," Macromol. Biosci. 2008, 8, 479-483 (Year: 2008).*

Wang Z et al: "Direct Electrochemical Reduction of Single-Layer Graphene Oxide and Subsequent Functionalization with Glucose Oxidase", Journal of Physical Chemistry C, vol. 113, No. 32, Aug. 13, 2009, pp. 14071-14075.

Shan C et al: "Electrochemical determination of NADH and ethanol based on ionic liquid-functionalized graphene", Biosensors and Bioelectronics, Elsevier BV, NL, vol. 25, No. 6, Feb. 15, 2010, pp. 1504-1508.

International Search Report dated Nov. 27, 2017, of the corresponding International Application PCT/EP2017/065777 filed Jun. 27, 2017.

Jackowska, et al., "New Trends in the Elechrochemical Sensing of Dopamine," Anal Bionanal Chem 405, pp. 3753-3771, (2013).

Bard et al., Electrochemical Methods: Fundamentals and Applications, John Wiley & Sons, 96-115, (2001).

K. Thomas Finley, "Quinones," Kirk-Othmer Encyclopedia of Chemical Technology, pp. 1-35, (2005).

Chambers, J.Q.,"Electrochemistry of quinones," Chemistry of Quinoid Compounds, 1, pp. 737-791, (1974).

Chambers, J.Q., "Electrochemistry of quinones," Chemistry of Quinoid Compounds, 2, pp. 719-757, (1988).

Chen et al., "Graphene oxide: preparation, functionalization, and electrochemical applications," Chemical Reviews, 2012,112, pp. 6027-6053.

Bae et al., "Enhanced electrochemical reactions of 1,4-benzoquinone at nanoporous electrodes," Phys. Chem. Chem. Phys., 15, pp. 10645-10653, (2013).

Rosokha et al., "Continuum of Outer- and Inner-Sphere Mechanisms for Organic Electron Transfer. Steric Modulation of the Precursor Complex in Paramagnetic (Ion-Radical) Self-Exchanges," J. Am. Chem. Soc., 129(12), pp. 3683-3697, (2007).

DuVall et al., "Control of Catechol and Hydroquinone Electron-Transfer Kinetics on Native and Modified Glassy Carbon Electrodes," Anal. Chem., 71(20), pp. 4594-4602, (1999).

DuVall, et al., "Self-catalysis by Catechols and Quinones during Heterogeneous Electron Transfer at Carbon Electrodes," J. Am. Chem. Soc., 122(28), pp. 6759-6764, (2000).

Marrikar et al., "Modification of Indium-Tin Oxide Electrodes with Thiophene Copolymer Thin Films: Optimizing Electron Transfer to Solution Probe Molecules," Langmuir, 23(3), pp. 1530-1542, (2007).

Quan et al., "Voltammetry of quinones in unbuffered aqueous solution: reassessing the roles of proton transfer and hydrogen bonding in the aqueous electrochemistry of quinones," J. Am. Chem. Soc. 2007,129(42), pp. 2847-2856.

Zudans et al., "Electrochemical and optical evaluation of noble metal- and carbon-ITO hybrid optically transparent electrodes," Journal of Electroanalytical Chemistry,565, 2004, pp. 311-320.

Chen et al., "Direct electrodeposition of reduced graphene oxide on glassy carbon electrode and its electrochemical application," Electrochemistry Communications, 13(2), pp. 133-137, (2011).

McGrail et al., "Rapid functionalization of graphene oxide in water," Chemistry of Materials, 2014, 26, pp. 5806-5811.

Georgakilas et al.,"Functionalization of raphene: covalent and non-covalent approaches, derivatives and applications," Chemical Review, 2012, 112, pp. 6156-6214.

Wang et al., "In situ electrochemical and surface plasmon resonance (SPR) studies of aniline-carboxylated aniline copolymers," Analytica Chimica Acta, (558), pp. 150-157, 2006.

McCullough, Richard D., "The chemistry of conducting polythiophenes," Advanced Materials, 1998, 10, No. 2, pp. 93-116.

McCullough et al., "Self-Assembly and disassembly of regioregular, water soluble polythiphenes: chemoselective ionchromatic sensing in water," J. Am. Chem. Soc., 1997, 119, pp. 633-634.

Chapman et al., "Preparation of mixed self-assembled monolayers (SAMs) that resist adsorption of proteins using the reaction of amines with a SAM that presents interchain carboxylic anhydride groups," Langmuir 2000, 16, pp. 6927-6936.

Alonso et al.,"Covalent attachment of 1-Alkenes to oxidized platinum surfaces," Langmuir 2015, 31, pp. 2714-2721.

Chapman et al., "Surveying for surfaces that resist the adsorption of proteins," J. Am. Chem. Soc. 2000, 122, pp. 8303-8304.

Abraham et al., "Molecularly engineered p(HEMA)-based hydrogels for implant biochips biocompatibility", Biomaterials, Elsevier Science Publishers BV., Barking, GB, vol. 26, No. 23, Aug. 1, 2005.

Kotanen et al., "Amperometric glucose biosensor based on electroconductive hydrogels", Talanta, vol. 103, Jan. 1, 2013, pp. 228-235.

* cited by examiner

ELECTRODE ARRANGEMENT WITH IMPROVED ELECTRON TRANSFER RATES FOR REDOX OF MOLECULES

FIELD OF INVENTION

Aspects of the present invention relate to electrode surface modifications and methods for modifying an electrode surface to optimize electron transfer kinetics in electrochemical systems, and particularly in systems with inherently slow electron transfer kinetics, such as systems that use quinones as redox molecules. Aspects of the invention also relate to application of these modifications to electrodes while maintaining the functionality of other surface modifications that the electrode contains.

BACKGROUND

Electrode composition is of great importance in an electrochemical system, particularly in biochemistry, such as a biosensor. First, the electrode materials should be biocompatible with each other, and should not interfere with the standard behavior of any components in the system via reaction or catalysis. Second, the potential window of the electrode must be wide enough to perform the desired electrochemistry without degrading the electrode. Third, the electrode should resist undesired modification from the system, such as from proteins, salts, or other chemical species irreversibly binding to the surface and reducing the amount of active surface area. Fourth, some electrochemical assays require the chemical species to be tethered closely to the electrode. Fifth, in some applications, certain optical properties of the electrode (such as transparency or opacity to certain wavelengths) may be required. Finally, the target electrochemistry reaction should ideally proceed at a potential that excludes unproductive and/or unintended side reactions with components of the system.

Electron transfer kinetics also play an important part in an electrochemical system. Fast electron transfer kinetics are highly advantageous in electrochemistry because they allow for rapid equilibrium of the overall system following a redox event (Bard et al., Electrochemical Methods: Fundamentals and Applications, John Wiley & Sons, 96-115 (2001)). For voltammetric sensing platforms, electron transfer kinetics translate directly as the lag time of the sensor, and faster kinetics yield a sensor that rapidly reflects the surrounding electrochemical environment. For electrodes that actively drive redox processes, faster kinetics allow for less activation overpotential, allowing redox to occur near the standard potential ($E^0$) of the target species. This can help reduce unwanted side reactions with other components of the system. In both cases, fast electron transfer kinetics help to make the electrochemical system respond predictably.

Electrode composition can affect electron transfer kinetics in an electrochemical system, and is of particular importance with respect to electrochemical species that do not undergo efficient electron transfer. In such systems, where additional processes are requisite for electron transfer (e.g., proton exchange, solvent reorganization, bond rearrangement, etc.) and substantially contribute to its rate, the Nernst equation does not apply effectively, and physical models built upon the Nernst equation are rendered inaccurate.

Quinones are an example of such electrochemical species that undergo inefficient electron transfer. Quinones are one of the most widely studied classes of electrochemically active molecules (see K. Thomas Finley, "Quinones," Kirk-Othmer Encyclopedia of Chemical Technology, 1-35 (2005), which is incorporated herein by reference in its entirety. See also, Chambers, J. Q., "Electrochemistry of quinones," Chemistry of Quinoid Compounds, 1:737-91 (1974); Chambers, J. Q., "Electrochemistry of quinones," Chemistry of Quinoid Compounds, 2:719-57 (1988); Evans, D. H., Encyclopedia of Electrochemistry of the Elements, 12:1-259 (1978)). Quinones are a large class of organic redox molecules that find frequent use in a wide range of electrochemical systems, including biological, synthetic, industrial, medicinal, and fundamental academic applications, but often have inherently sluggish electron transfer rates to many electrodes.

Two broad factors contribute to these slow electron transfer rates for quinones. First, quinones undergo a two-proton, two-electron redox reaction. Thus, their voltammetric behavior is dictated by additional factors arising from proton transfer, including diffusion coefficients, temperature, pKa values for the relevant species, stability of the dianion, and possibly proton transfer rate constants (see Bae et al., "Enhanced electrochemical reactions of 1,4-benzoquinone at nanoporous electrodes," Phys. Chem. Chem. Phys., 15:10645-53 (2013)). As a result, quinones do not conform to standard Nernstian behavior, necessitating large overpotentials at most electrodes to initiate redox, thus limiting their utility as potentiometric sensors. While structural changes to the quinone molecule can help to tune this inherent speed, such changes inevitably have other consequences on the molecular behavior as well (including shifted standard potential ($E^0$), changes to solubility, etc.), and these additional consequences are often significant and cannot be generalized.

Second, quinones must be physically adjacent to the electrode before electron transfer can occur, as quinones undergo quasi-inner sphere electron transfer (Type M in the Robin-Day classification system) (see Rosokha et al., "Continuum of Outer- and Inner-Sphere Mechanisms for Organic Electron Transfer. Steric Modulation of the Precursor Complex in Paramagnetic (Ion-Radical) Self-Exchanges," J. Am. Chem. Soc., 129(12):3683-97 (2007)). Thus, the electrode surface can introduce several additional factors that can reduce the observed electron transfer of the quinones from its optimal rate. For example, steric crowding at the electrode interface can have very significant effects (see DuVall et al., "Control of Catechol and Hydroquinone Electron-Transfer Kinetics on Native and Modified Glassy Carbon Electrodes," Anal. Chem., 71(20):4594-4602 (1999)). Likewise, the electrostatic charge on the electrode surface can attract or repel quinones, and thereby exert a large influence on the electron transfer rate (see DuVall, et al., J. Am. Chem. Soc., 122(28):6759-64 (2000)). The diffusion rate of quinones and the variables that affect it (e.g., temperature, viscosity, etc.) can also impact electron transfer. Additionally, the overall surface area of the electrode is an important determinant in how much electron transfer is accomplished. For example, some electrodes, like indium tin oxide (ITO) electrodes, are further handicapped in that only a fraction of their surface area is actually electrochemically active. The vast majority of the physical interface of an ITO electrode is not conductive, as there are only small hot spots that are conductive and permit reactions to occur (see Marrikar et al., "Modification of Indium-Tin Oxide Electrodes with Thiophene Copolymer Thin Films: Optimizing Electron Transfer to Solution Probe Molecules," Langmuir, 23(3):1530-42 (2007)). Thus, redox molecules, such as quinones, only react when in contact with one of the hot spots on the electrode, resulting in an even more inefficient electron transfer reaction.

Methods of improving electron transfer from an electrode to a target species are known. Electronic biochemical sensors can use an enzyme that oxidizes or reduces the target molecule, and then an electrode "regenerates" the enzyme by reducing or oxidizing it (respectively), and the total current passed by the electrode is used to quantify the amount of target molecule present. However, the enzyme is often a poor electron transfer partner with the electrode, so organic molecules are utilized as mediators, or shuttles, to help transfer the electron. U.S. Pat App. Pub. No. 2006/0113187 discloses that ruthenium, ferrocene, or ferricyanide derivatives can be employed in the solution to enhance electron transfer. U.S. Pat. Nos. 4,879,243 and 7,544,438 disclose that quinone derivatives can fulfill this function, but the electron transfer mediators/enhancers are dissolved into the analytical solution itself, and not localized onto the electrode. U.S. Pat. No. 7,384,749 discloses that the electron transfer enhancer/moiety (such as ferrocene) can be affixed to the target molecule for site-selective modification of nucleic acids. EP0187719 discloses utilizing a small molecule ((pyridinyl-methylene)hydrazinecarbothioamide (PHMC)) bound to the electrode surface to enhance electron transfer to species in solution without using an intermediary mediator. Organic layers can also be utilized in solar cell applications to enhance the conductivity between two electrode materials.

SUMMARY

A summary of certain example embodiments of the present invention is set forth below. It should be understood that these aspects are presented merely to provide the reader with a brief summary of these certain embodiments and that these aspects are not intended to limit the scope of the present invention. Indeed, this invention can encompass a variety of aspects that may not be set forth below.

Example embodiments of the present invention provide biochemical systems with modifications or coatings to electrodes that improve electron transfer from an electrode to a target species, but without disrupting the functionality of any other modifications or coatings on the electrode. For example, an electrode can contain a coating of a hydrophilic polymer, such as polyethylene glycol (PEG), on its surface. Conventional polymer coatings, through their attached reactive groups, immobilize biomolecules of interest from a solution. According to example embodiments of the present invention, the coating or modification to improve electron transfer does not deactivate or otherwise interfere with the reactive groups of the polymer coating in a manner that disrupts immobilization of the biomolecules of interest onto the polymer coating.

Such electrode coatings have been described for determining the presence and/or amount of unknown quinones or quinone derivatives, such as dopamine, in a biological sample in Jackowska et al., "New trends in the electrochemical sensing of dopamine," Anal. Bioanal. Chem., 405:3753-71 (2013), and in the publications cited within Jackowska et al.

Thus, embodiments of the present invention provide for modification of an electrode surface to optimize electron transfer kinetics in electrochemical systems that feature inherently slow electron transfer kinetics (such as those involving quinones), without altering the chemical structure of the redox molecule itself. Example embodiments of the present invention apply such modifications to an electrode without disrupting the functionality of any other electrode modifications.

Example embodiments of the present invention provide electrodes, and methods for making modified electrodes, with improved electron transfer rates to redox molecules. In an example embodiment, these modified electrodes are used in a biochemical platform with additional requirements to preserve certain optical properties and chemical interfaces of the original electrode. Such modified electrodes can be utilized in systems for pH sensing and/or pH modulation and in biosensor systems as described in U.S. patent application Ser. Nos. 14/792,553, 14/792,576, 14/792,541, 14/792,569, and 14/792,530, which are hereby incorporated herein by reference in their entireties.

According to an example embodiment of the present invention, a biosensor is provided that includes one or more regions, where each region is configured to control its own local pH level, such that each region can have a different pH level. According to an example embodiment, different regions of the sensor are provided for detecting the presence or specific concentration(s) of one or more respective proteins at that region's particular local pH level. The presence of the one or more respective proteins, or a combination of the presence of different proteins, or specific concentration(s) thereof, at each region creates a unique signature or profile. For example, according to an example embodiment, by detecting the presence of a particular protein at multiple pH levels, a unique profile or signature for how that protein responds to a broad range of pH levels is obtained. When a signal is measured for a sample that contains multiple proteins at the different pH levels, the resulting dataset contains multiple profiles, but the unique profile of a protein of interest can be isolated at higher fidelity from this larger dataset A unique signature or profile can signal the presence of a corresponding condition, e.g., a disease. In an example embodiment, the biosensor thereby detects whether the condition is present and includes an output interface for outputting a signal, e.g., a binary signal, indicating whether the condition is present. The ability to manipulate and control pH levels at different regions of the sensor allows for a better sensor.

In order for the sensor to properly detect the presence or concentration(s) of the one or more proteins to obtain the signature or profile, in an example embodiment, the sensor includes, at each protein sensing region, one or more electrodes and also quinones for establishing the pH level at each respective region. The quinones can be attached to the surface of the electrode or, more preferably, included in a solution with which the electrodes are in contact, and by which solution changes in pH level can be sustained due to replacement of spent quinones with fresh qinones of the solution. Each electrode is charged at a particular voltage or current, thereby activating (e.g., oxidizing or reducing) the quinones to produce the necessary reaction (e.g., electron transfer between the quinones and electrode) to establish the local pH level.

Quinones have an inherent voltage at which they are activated to allow electron transfer to occur. Quinones also undergo a two-proton, two-electron redox reaction. Because of these unique properties of quinones, in an example embodiment, the biosensor uses the quinones to both sense the pH level and also regulate the pH level at an electrode, and then re-regulate the pH level based on the sensed pH level. In one example embodiment, a charge is applied to the electrode at a certain current, and by measuring the resulting voltage at which electron transfer occurs between the quinones and electrode, the local pH at that electrode is determined. In another example embodiment, a charge is applied to the electrode at a certain voltage, and by measuring the resulting current at which the electron transfer occurs, the local pH at that electrode is determined.

In an example embodiment using a closed system, a single electrode is used to sense the pH levels and regulate the pH levels by activating the quinones. In another example embodiment, one electrode or set of electrodes is used to sense the pH levels, and another electrode or set of electrodes is used to regulate the pH levels.

Regulation and/or sensing of pH levels using quinones is optimal when the quinones are activated to allow electron transfer at or close to their inherent voltage. If electron transfer inefficiencies exist, such as the presence of an electrode that is less conductive (like an ITO electrode), the charge required for activating quinones to allow electron transfer may be greater than the inherent voltage of the quinones (i.e., an overpotential). Overpotential is problematic in that it is not predictable. Overpotential can also cause a lag in the pH level sensing and regulation, rendering the biosensor less reliable and less accurate. Further, overpotential can negatively affect other materials of the biosensor, such as DNA, also rendering the biosensor less reliable and less accurate.

Thus, according to example embodiments of the present invention, a coating is applied to an electrode that increases electron transferability between the surface of the electrode and quinones, to the extent that allows the quinones to be activated for regulating and/or sensing the pH levels at their inherent voltage. The coating is applied in addition to another coating that is configured to immobilize biomolecules for detecting the presence or specific concentration(s) of the biomolecules. The coating for increasing electron transferability is applied in a particular manner such that it does not inhibit the functionality of the other coating configured to immobilize biomolecules. In this regard, in an example embodiment, the coating for biomolecule immobilization is applied in a sparse manner with voids, and the coating for increasing electron transferability is applied in those voids, and, in an example embodiment, at a thickness that is less than the thickness of the coating configured to immobilize biomolecules, thereby allowing the coating configured to immobilize biomolecules to extend beyond coating for increasing electron transferability. This example embodiment allows the coating for increasing electron transferability to be applied to a slide (that has one or more electrodes) that already has on it the coating for biomolecule immobilization. In an alternative example embodiment, a slide (that has one or more electrodes) is obtained without the coating for biomolecule immobilization, the coating for increasing electron transferability is applied to the slide, and subsequently the coating for biomolecule immobilization is applied on top of the coating that increases electron transferability, so that the coating for biomolecule immobilization is unimpeded by the coating that increases electron transferability. In either embodiment, if necessary, after applying the coating for increasing electron transferability to the slide, the coating can be patterned or etched such that the coating is limited to just the one or more electrodes.

According to example embodiments, there is provided a coated electrode comprising: (a) an electrode; (b) a coating configured to immobilize biomolecules; and (c) a coating configured to improve electron transfer rate.

In some example embodiments, the electrode is an ITO electrode.

In some example embodiments, the coated electrode is configured to activate a quinone to regulate or sense a pH level in a region local to the coated electrode.

In some example embodiments, the coating configured to immobilize biomolecules comprises poly(ethylene glycol) carboxymethyl succinimidyl ester (PEG-NHS) polymers.

In some example embodiments, the coating configured to immobilize biomolecules contains gaps in between each of the PEG-NHS polymers.

In some example embodiments, the coating configured to improve electron transfer rate is deposited in the gaps in between each of the PEG-NHS polymers, such that the two coatings are interspersed among each other.

In some example embodiments, a thickness of the coating configured to improve electron transfer rate is less than a thickness of the coating configured to immobilize biomolecules.

In some example embodiments, the coating configured to improve electron transfer rate contains one or more chemical handles, where the one or more chemical handles are configured to bind the coating configured to immobilize biomolecules to the coating configured to improve electron transfer rate.

In some example embodiments, the one or more chemical handles are selected from a group consisting of carboxylates, amines, and thiols.

In some embodiments, the coating configured to improve electron transfer rate is made entirely or substantially of conductive organic polymers.

In some example embodiments, the conductive organic polymers are selected from a group consisting of polyanilines, polythiophenes, polypyrroles, polyindoles, and polyphenylenes.

In some example embodiments, the coating configured to improve electron transfer rate is made entirely or substantially of an inorganic conductive material.

In some example embodiments, the inorganic conductive material includes nanoparticles.

In some example embodiments, the inorganic conductive material is selected from a group consisting of gold, platinum, and palladium.

In some example embodiments, a thickness of the coating configured to improve electron transfer rate is less than 100 nanometers.

In some example embodiments, the coating configured to improve electron transfer rate is made entirely or substantially of graphene.

According to example embodiments, there is provided a biosensor that includes a plurality of electrodes, each electrode being a coated electrode that includes: (a) an electrode; (b) a coating configured to immobilize biomolecules; and (c) a coating configured to improve electron transfer rate.

According to example embodiments, there is provided a method of modifying an electrode, the method including: (a) providing an electrode with a coating configured to immobilize biomolecules via one or more chemical groups; and (b) applying to the electrode a coating configured to improve electron transfer rate.

In some example embodiments, the coating configured to immobilize biomolecules includes PEG-NHS polymers.

In some example embodiments, the electrode is an ITO electrode.

In some example embodiments, the coating configured to improve electron transfer rate is made entirely or substantially of conductive organic polymers.

In some example embodiments, the conductive organic polymers are selected from a group consisting of polyanilines, polythiophenes, polypyrroles, polyindoles, and polyphenylenes.

According to example embodiments, there is provided a method of modifying an electrode, the method including: (a) providing an electrode with a coating configured to immobilize biomolecules via one or more chemical groups; (b) inactivating the one or more chemical groups of the coating configured to immobilize biomolecules; (c) applying to the electrode a coating configured to improve electron transfer rate; and (d) reactivating the one or more chemical groups. In an example embodiment, the application of the coating occurs subsequent to the inactivating and prior to the reactivating.

In some example embodiments, the one or more chemical groups are deactivated using hydrolysis.

In some example embodiments, the coating configured to improve electron transfer rate is applied using electropolymerization.

In some example embodiments, the coating configured to improve electron transfer rate is made entirely or substantially of an inorganic conductive material.

In some example embodiments, the inorganic conductive material includes nanoparticles.

In some example embodiments, the inorganic conductive material is selected from a group consisting of gold, platinum, and palladium.

In some example embodiments, the coating configured to improve electron transfer rate is applied using a technique selected from a group consisting of vapor-phase deposition, electroplating, electrodeposition, and solution-phase deposition.

In some example embodiments, a thickness of the coating configured to improve electron transfer rate is less than 100 nanometers.

In some example embodiments, the coating configured to improve electron transfer rate is made entirely or substantially of graphene.

In some example embodiments, the coating configured to improve electron transfer rate is applied using electrodeposition or covalent attachment.

According to example embodiments, there is provided a method of modifying an electrode, the method comprising: (a) providing an electrode; (b) applying to the electrode a coating configured to improve electron transfer rate; (c) incorporating one or more chemical handles onto the coating configured to improve electron transfer rate; and (d) applying to the electrode a coating configured to immobilize biomolecules, where the one or more chemical handles are configured to bind the coating configured to immobilize biomolecules to the coating configured to improve electron transfer rate.

In some example embodiments, the coating configured to immobilize biomolecules includes PEG-NHS polymers.

In some example embodiments, the electrode is an ITO electrode.

In some example embodiments, the one or more chemical handles are selected from a group consisting of carboxylates, amines, and thiols.

In some example embodiments, the coating configured to improve electron transfer rate is made entirely or substantially of conductive organic polymers.

In some example embodiments, the conductive organic polymers are selected from a group consisting of polyanilines, polythiophenes, polypyrroles, polyindoles, and polyphenylenes.

In some example embodiments, the coating configured to improve electron transfer rate is made entirely or substantially of an inorganic conductive material.

In some example embodiments, the inorganic conductive material is platinum or palladium.

In some example embodiments, the coating configured to improve electron transfer rate is made entirely or substantially of graphene.

According to example embodiments, there is provided a method comprising: contacting a coated electrode with a solution that includes a quinone, where the coated electrode includes (a) an electrode, (b) a coating configured to immobilize biomolecules, and (c) a coating configured to improve electron transfer rate; applying a charge to the coated electrode to activate the quinone; measuring a pH level of a region local to the coated electrode; and adjusting the pH level.

These and other features, aspects, and advantages of the present invention will become better understood when the following detailed description of certain exemplary embodiments is read with reference to the accompanying drawings in which like characters represent like parts throughout the drawings.

DETAILED DESCRIPTION

Example embodiments of the present invention provide electrodes modified to improve electron transfer rates between the electrode and redox molecules, particularly redox molecules with inherently slow electron transfer rates (such as quinones), by the addition of different materials that increase the electrically conductive surface area of the electrode. Such modifications are applied to the electrode while preserving the functionality of other surface characteristics of the electrode, such as immobilization of biomolecules by a polymer coating.

Figure 1:
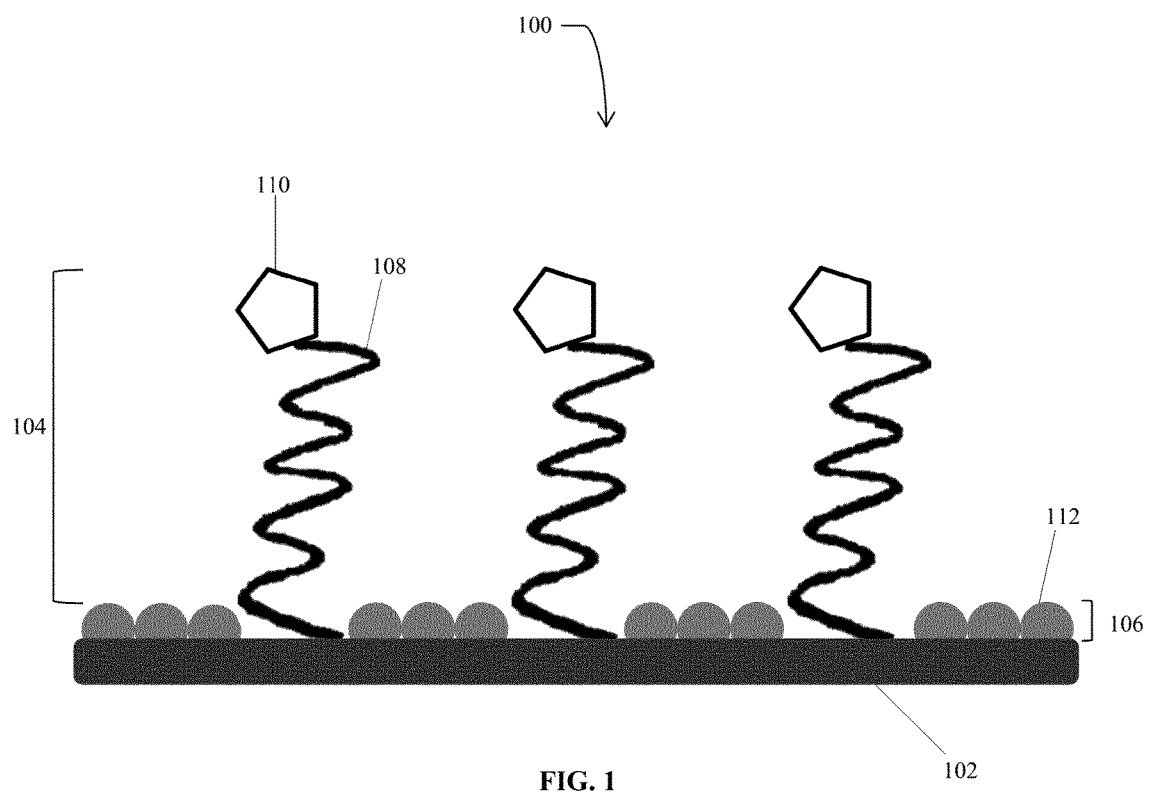
FIG. 1 illustrates a coated electrode according to an example embodiment of the present invention.

FIG. 1 shows a coated electrode 100 that includes electrode 102, a coating 104 configured to immobilize biomolecules, and a coating 106 configured to improve electron transfer rate. Electrode 102 can be included on a substrate, such as a slide. Electrode 102 can be any electrode suitable in a biosensor, for example an ITO, gold, or silver electrode. In a preferred example embodiment, electrode 102 is an ITO electrode. ITO is a transparent conductor. As opposed to gold or platinum, ITO conducts electricity while remaining transparent. Transparency may be important, particularly in biological and biochemical platforms where optical techniques are employed, and ability to see through a slide is imperative. Coated electrode 100 can be used in a solution that includes a predetermined concentration and amount of quinones. Coated electrode 100 can be used to activate a quinone to regulate or sense a pH level in a region local to the coated electrode 100. Coated electrode 100 can be used as part of a sensor or actuator or both, for the purpose of sensing and/or modulating pH levels of the solution local to the coated electrode 100. In an example embodiment, the coating 104 configured to immobilize biomolecules includes hydrophilic polymers 108, such as PEG, with each of the polymers 108 being functionalized with a functional group 110 for conjugation of biomolecules. The functional group 110 can include, for example, NHS, maleimide, fluorophenyl, carbamates, carbonates, epoxides, aldehydes, and azlactone. For example, U.S. patent application Ser. No. 15/169,008, filed May 31, 2016, which is hereby incorporated by reference in its entirety, discloses azlactone functionalized substrates for conjugation of biomolecules.

As shown in FIG. 1, the coating 106 configured to improve electron transfer rate can be made of conductive organic polymers 112, such as polyanilines, polythiophenes, polypyrroles, polyindoles, and polyphenylenes. Such organic conductive polymers 112 can increase the working area of a 2D electrode by creating a high-density, 3D conductive surface. While most of these organic conductive polymers will yield a spectroscopic signature, a thin layer will not affect bulk optical properties such as transparency and reflectivity.

As shown in FIG. 1, according to one example embodiment, the coating 104 configured to immobilize biomolecules contains gaps in between each of the functionalized hydrophilic polymers 108. The coating 106 configured to improve electron transfer rate is deposited in the gaps in between each of the hydrophilic polymers 108, such that coating 106 and coating 104 are interspersed among each other. In this example embodiment, a thickness of the coating 106 configured to improve electron transfer rate is less than the thickness of the coating 104 configured to immobilize biomolecules. Having coating 106 interspersed among coating 104 and the difference in thickness will ensure that each coating functions properly without interfering with the other coating's functionality. Coating 106 can improve the electron transfer rate while allowing coating 104 to conjugate biomolecules, since functional groups 110 remain accessible to biomolecules.

Figure 2:
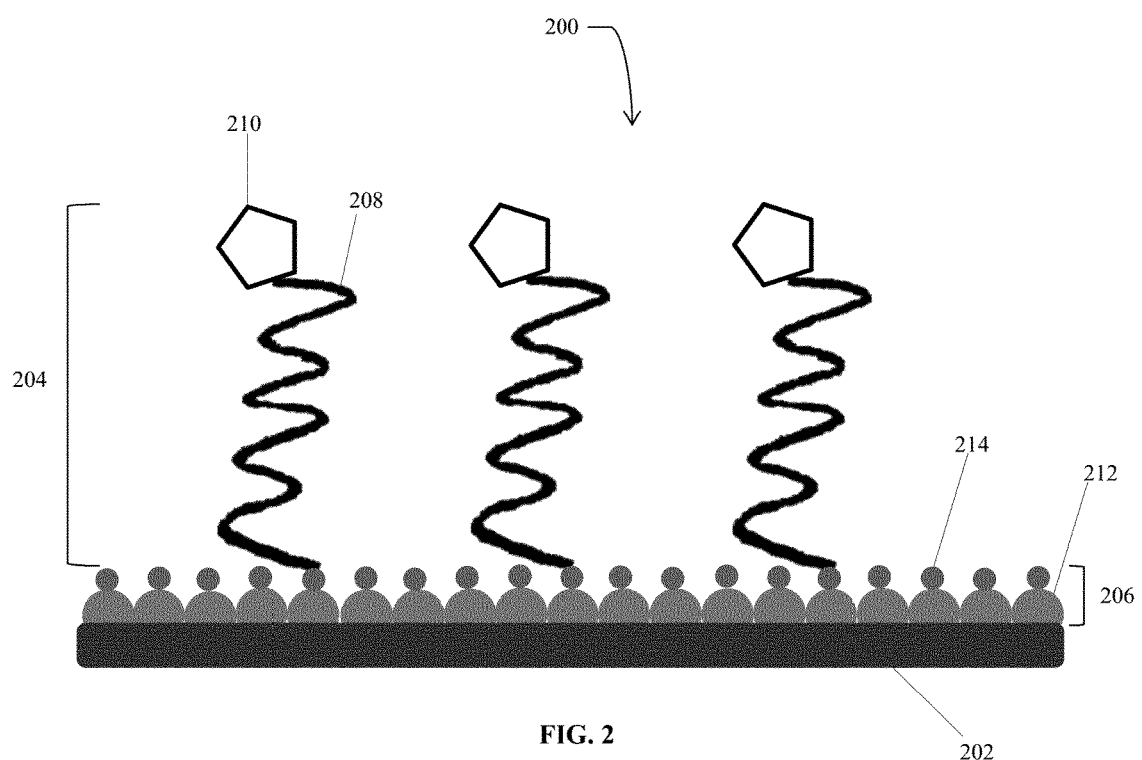
FIG. 2 illustrates a coated electrode according to another example embodiment of the present invention.

FIG. 2 shows another example embodiment of a coated electrode 200 that is similar to FIG. 1. Coated electrode 200 includes an electrode 202, a coating 204 configured to immobilize biomolecules, and a coating 206 configured to improve electron transfer rate. The coating 204 configured to immobilize biomolecules is made of hydrophilic polymers 208 functionalized with functional groups 210 for conjugation of biomolecules. The coating 206 configured to improve electron transfer rate can be made of conductive organic polymers 212. In FIG. 2, the coating 206 configured to improve electron transfer rate contains chemical handles 214 configured to bind the coating 204 configured to immobilize biomolecules to the coating 206 configured to improve electron transfer rates. The chemical handles 214 can be carboxylates, amines, or thiols. One way in which the embodiment shown in FIG. 2 differs from the embodiment shown in FIG. 1 is that in FIG. 2, coating 206 is deposited onto electrode 202 (which can be included on another substrate, such as a slide) prior to deposition of coating 204. In FIG. 1, coating 106 can be deposited onto electrode 102 (which can also be included on another substrate, such as a slide) where electrode 102 already includes coating 104.

According to another example embodiment of the present invention, the coating 106/206 configured to improve electron transfer rate is made of inorganic conductive material, such as gold, platinum, or palladium. The inorganic conductive material can be in the form of nanoparticles. For a sparsely conductive surface like an ITO electrode, a thin (less than 100 nm) coating of carbon, platinum, palladium, or gold can dramatically increase the conductive surface area from just the discrete hot spots to the entire surface.

According to another example embodiment of the present invention, the coating 106/206 configured to improve electron transfer rate is made of graphene. Even simple monolayers of graphene are highly conductive, and they can help to convert a sparsely active surface, like an ITO electrode, into a fully conductive one. Graphene also interacts favorably with organic redox reagents like quinones, which helps to increase the turnover rate of the quinones (i.e., increase the electron transfer efficiency).

Figure 3:
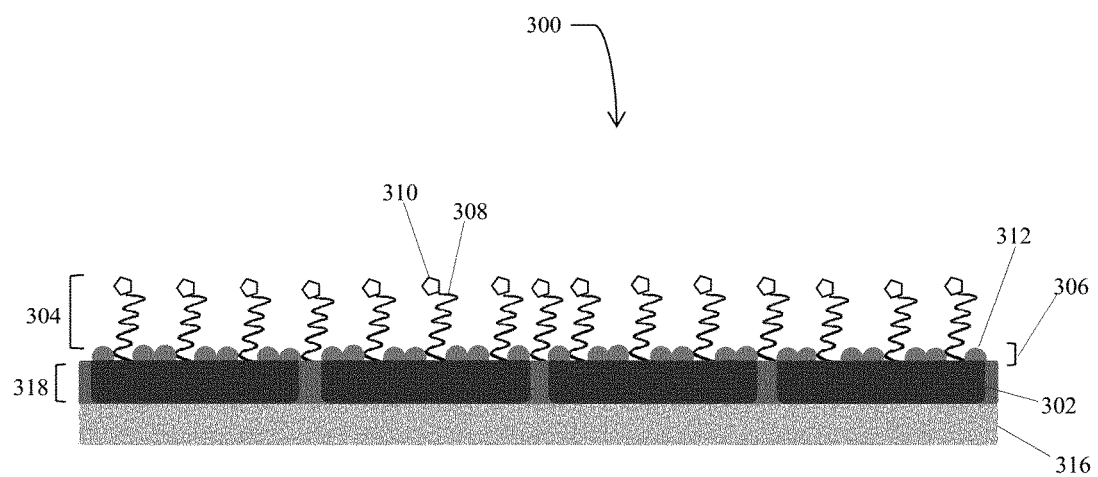
FIG. 3 illustrates a biosensor including a plurality of coated electrodes, according to an example embodiment of the present invention.
Figure 4:
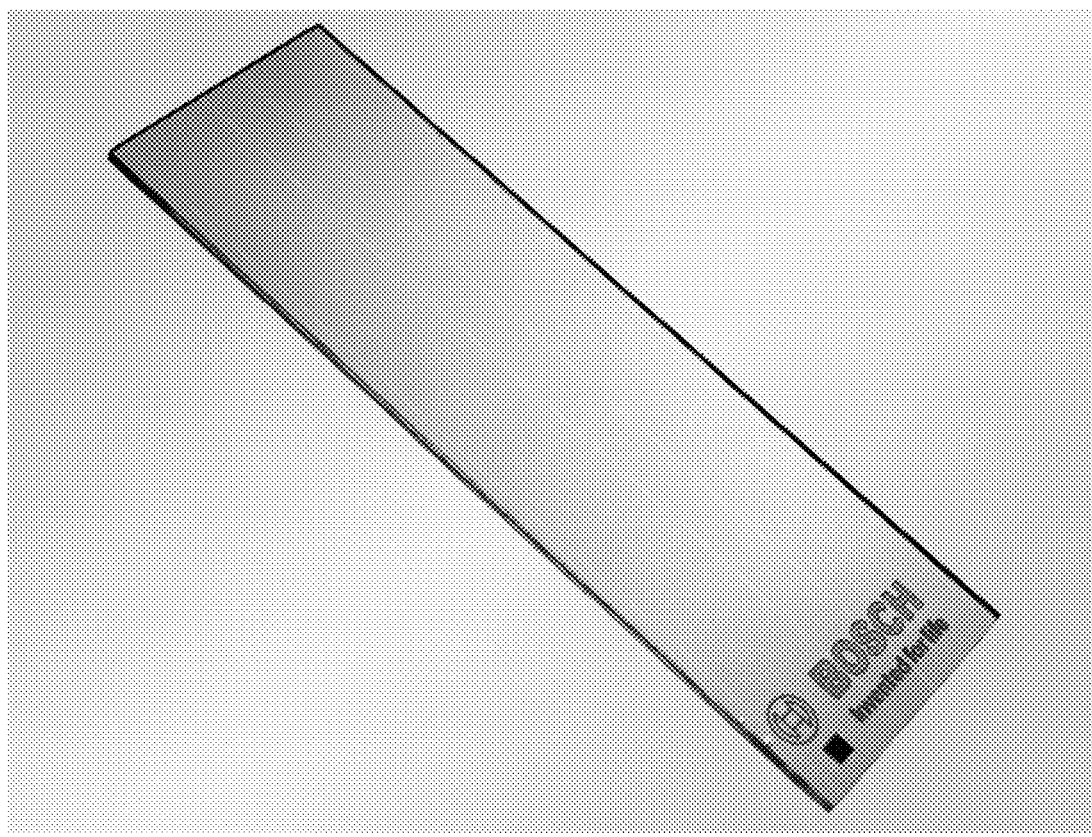
FIG. 4 shows a glass slide with an ASIC chip interfaced to transparent ITO electrodes.

FIG. 3 shows a biosensor 300 that includes a plurality of electrodes 318 attached to a substrate 316, where each electrode 302 is a coated electrode similar to the coated electrode 100 of FIG. 1, with a coating 304 configured to immobilize biomolecules and a coating 306 configured to improve electron transfer rate. The coating 304 configured to immobilize biomolecules is made of hydrophilic polymers 308 functionalized with functional groups 310 for conjugation of biomolecules. The coating 306 configured to improve electron transfer rate can be made of conductive organic polymers 312. FIG. 3 shows an embodiment similar to FIG. 1, where the coating 304 configured to immobilize biomolecules contains gaps in between each of the functionalized hydrophilic polymers 308, and the coating 306 configured to improve electron transfer rate is deposited in the gaps in between each of the hydrophilic polymers 308, such that coating 306 and coating 304 are interspersed among each other and such that a thickness of coating 306 is less than the thickness of coating 304.

In another embodiment, a biosensor includes a plurality of electrodes attached to a substrate, where each electrode is a coated electrode similar to the coated electrode of FIG. 2. In this embodiment, the coating configured to improve electron transfer rate contains chemical handles configured to bind the coating configured to immobilize biomolecules to the coating configured to improve electron transfer rate. In this embodiment, the coating configured to improve electron transfer rate is deposited prior to deposition of the coating configured to immobilize biomolecules.

According to example embodiment of the present invention, a method includes modifying, or applying a coating to, electrodes for the purpose of improving electron transfer rates between the electrodes and redox molecules, particularly redox molecules with inherently slow electron transfer rates (such as quinones). Such a modification or coating is applied without disturbing the existing chemical interfaces on the electrode surface, such as an existing polymer coating configured to immobilize biomolecules. Alternatively, the modification or coating is applied such that chemical interfaces can be constructed following application. In an example embodiment, the existing polymer coating configured to immobilize biomolecules is made of hydrophilic polymers, such as PEG, and each polymer is functionalized with a functional group for conjugation of biomolecules, where such functional groups include NHS, maleimide, fluorophenyl, carbamates, carbonates, epoxides, aldehydes, or azlactone. The electrode can be any electrode suitable in a biosensor, for example an ITO, gold, or silver electrode. In a preferred example embodiment, the electrode is an ITO electrode.

According to an example embodiment, when applying a coating that is configured to improve electron transfer rate that is made entirely or substantially of conductive organic polymers, in order to preserve chemical interfaces, a method of modifying the electrode includes: (a) providing an electrode with a coating configured to immobilize biomolecules via one or more chemical groups; (b) then inactivating the one or more chemical groups of the coating configured to immobilize biomolecules; (c) then applying to the electrode a coating configured to improve electron transfer rate; and (d) then reactivating the one or more chemical groups. This method can be particularly effective for preserving chemical interfaces that are designed to covalently bind proteins or other solution components to the surface of the electrode. In this embodiment, a thickness of the coating configured to improve electron transfer rate is less than a thickness of the coating configured to immobilize biomolecules. In an example embodiment, the deactivation of the one or more chemical groups is performed using hydrolysis. If required, any remaining reactivity of the chemical groups can be furthered reduced using protecting groups, which are known.

According to another example embodiment, when applying a coating that is configured to improve electron transfer rate that is made entirely or substantially of conductive organic polymers, in order to preserve chemical interfaces, a method of modifying the electrode includes: (a) providing an electrode with a coating configured to immobilize biomolecules via one or more chemical groups; and (b) applying to the electrode a coating configured to improve electron transfer rate, where the coating configured to improve electron transfer rate can be applied using electropolymerization. This method can be particularly effective for preserving chemical interfaces that are designed to reduce nonspecific adsorption to the surface of the electrode. Organic monomers can freely diffuse into the existing coating configured to immobilize biomolecules, and form the conductive organic polymers (i.e., the coating configured to improve electron transfer rate) after a charge is applied to the electrode and the monomers experience oxidative potentials near the electrode or polymer surface. In this embodiment, a thickness of the coating configured to improve electron transfer rate is less than a thickness of the coating configured to immobilize biomolecules.

In both methods provided for modifying an electrode by applying a coating configured to improve electron transfer rate, the coating including conductive organic polymers, the conductive polymers can be polyanilines, polythiophenes, polypyrroles, polyindoles, polyphenylenes, or mixtures thereof. These polymers can be assembled via electropolymerization, or via other standard polymer synthesis techniques. These polymers preserve the optical properties, such as transparency, of the electrode.

According to another example embodiment, when applying a coating configured to improve electron transfer rate that is made entirely or substantially of conductive organic polymers, in order to preserve chemical interfaces, a method of modifying an electrode includes: (a) providing an electrode; (b) applying to the electrode a coating configured to improve electron transfer rate; (c) incorporating one or more chemical handles onto the coating configured to improve electron transfer rate; and (d) applying to the electrode a coating configured to immobilize biomolecules, where the one or more chemical handles are configured to bind the coating configured to immobilize biomolecules to the coating configured to improve electron transfer rate. This method can be particularly effective for preserving chemical interfaces that are designed to reduce nonspecific adsorption to the surface of the electrode. The one or more chemical handles can be carboxylates, amines, and thiols. From the chemical handles, the full library of polymer synthesis techniques are available for applying the coating configured to immobilize biomolecules.

In another example embodiment, a method of modifying an electrode includes: (a) providing an electrode with a coating configured to immobilize biomolecules via one or more chemical groups; and (b) applying to the electrode a coating configured to improve electron transfer rate, where the coating configured to improve electron transfer rate is made of inorganic conductive material, such as gold, platinum, or palladium, which can be in the form of nanoparticles. The coating preserves the optical properties of the electrodes (such as transparency). The coating can be a thin film (less than 100 nanometers) that is applied via vapor-phase deposition, electroplating, electrodeposition, or solution-phase deposition. The coating can also be a sparse coating of nanoparticles or roughened nanoparticles, such as gold nanoparticles, which are deposited via electrodeposition. When applying gold nanoparticles, these nanoparticles can be electrodeposited directly onto an electrode surface from an $HAuCl_4$ solution without disturbing any existing chemical interfaces. The gold nanoparticles can be further roughened via electrode-induced oxidative processes, effectively creating a 3D interface with very high surface area (see Bae et al., "Enhanced electrochemical reactions of 1,4-benzoquinone at nanoporous electrodes," Physical Chemistry Chemical Physics, 15:10645-53 (2013)). Although higher concentrations of gold nanoparticles exhibit plasmonic behavior that can add optical artifacts to the electrode, lower concentrations should provide minimal disruption.

When applying platinum or palladium, since an electrode takes on the electronic properties of the top coating material, while largely preserving the optical properties of the underlying material (see Zudans et al., "Electrochemical and optical evaluation of noble metal- and carbon-ITO hybrid optically transparent electrodes," Journal of Electroanalytical Chemistry, 565(2):311-20 (2004)), adjustments to surface chemistry can be made to preserve any existing chemical interfaces, such as those configured to conjugate biomolecules (e.g., the functional groups on the PEG). Thus in another example embodiment, a method of modifying an electrode includes: (a) providing an electrode; (b) applying to the electrode a coating configured to improve electron transfer rate; (c) incorporating one or more chemical handles onto the coating configured to improve electron transfer rate; and (d) applying to the electrode a coating configured to immobilize biomolecules, where the one or more chemical handles are configured to bind the coating configured to immobilize biomolecules to the coating configured to improve electron transfer rate. In this example embodiment, the coating configured to improve electron transfer rate is made entirely or substantially of platinum or palladium. The coating preserves the optical properties of the electrodes (such as transparency). The coating can be a thin film (less than 100 nanometers) that is applied via vapor-phase deposition, electroplating, electrodeposition, or solution-phase deposition.

In an example embodiment, a method of modifying an electrode includes: (a) providing an electrode with a coating configured to immobilize biomolecules via one or more chemical groups; and (b) applying to the electrode, that already includes the biomolecule immobilization coating, a second coating, the second coating being configured to improve electron transfer rate, where the coating configured to improve electron transfer rate is made entirely or substantially of graphene. The graphene coating can be applied using electrodeposition from a graphene oxide solution via reductive potentials (see Chen et al., "Direct electrodeposition of reduced graphene oxide on glassy carbon electrode and its electrochemical application," Electrochemistry Communications, 13(2):133-37 (2011)) or by covalent attachment directly to the electrode surface in its oxidized form via standard coupling chemistries. Graphene largely preserves the optical properties of the electrodes (such as transparency).

Graphene can also be modified to preserve chemical interfaces, including the use of chemistries to open functional or chemical handles that can tether the desired chemical interface. Thus, in another example embodiment, a method of modifying an electrode includes: (a) providing an electrode; (b) applying to the electrode a coating configured to improve electron transfer rate; (c) incorporating one or more chemical handles onto the coating configured to improve electron transfer rate; and (d) applying to the electrode a coating configured to immobilize biomolecules, where the one or more chemical handles are configured to bind the coating configured to immobilize biomolecules to the coating configured to improve electron transfer rate. In this example embodiment, the coating configured to improve electron transfer rate is made entirely or substantially of graphene. The graphene coating can be applied using electrodeposition or by direct covalent attachment to the electrode.

The above description is intended to be illustrative, and not restrictive. Those skilled in the art can appreciate from the foregoing description that the present invention may be implemented in a variety of forms, and that the various embodiments can be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and the following claims.

What is claimed is:

1. A coated electrode comprising:
   (a) an electrode;
   (b) a coating configured to immobilize biomolecules; and
   (c) a coating configured to improve electron transfer rate;
   wherein one or both of the following:
      (1) the coated electrode further comprises (d) a quinone that the electrode is configured to trigger to regulate or sense a pH level in a region local to the coated electrode; and
      (2) the coating configured to immobilize biomolecules comprises poly(ethylene glycol) carboxymethyl succinimidyl ester (PEG-NHS) polymers.

2. The coated electrode of claim 1, wherein the electrode is an indium tin oxide electrode.

3. The coated electrode of claim 1, wherein the coated electrode is configured to activate a quinone to regulate or sense a pH level in a region local to the coated electrode.

4. The coated electrode of claim 1, wherein the coated electrode further comprises the quinone that the electrode is configured to trigger to regulate or sense the pH level in the region local to the coated electrode.

5. The coated electrode of claim 1, wherein the coating configured to immobilize biomolecules comprises the poly(ethylene glycol) carboxymethyl succinimidyl ester (PEG-NHS) polymers.

6. The coated electrode of claim 5, wherein the coating configured to immobilize biomolecules contains gaps in between each of the poly(ethylene glycol) carboxymethyl succinimidyl ester (PEG-NHS) polymers.

7. The coated electrode of claim 6, wherein the coating configured to improve electron transfer rate is deposited in the gaps in between each of the poly(ethylene glycol) carboxymethyl succinimidyl ester (PEG-NHS) polymers, such that the two coatings are interspersed among each other.

8. The coated electrode of claim 7, wherein a thickness of the coating configured to improve electron transfer rate is less than a thickness of the coating configured to immobilize biomolecules.

9. The coated electrode of claim 1, wherein the coating configured to improve electron transfer rate contains one or more chemical handles, and wherein the one or more chemical handles are configured to bind the coating configured to immobilize biomolecules to the coating configured to improve electron transfer rate.

10. The coated electrode of claim 9, wherein the one or more chemical handles are selected from a group consisting of carboxylates, amines, and thiols.

11. The coated electrode of claim 1, wherein the coating configured to improve electron transfer rate is made entirely or substantially of conductive organic polymers.

12. The coated electrode of claim 11, wherein the conductive organic polymers are selected from a group consisting of polyanilines, polythiophenes, polypyrroles, polyindoles, and polyphenylenes.

13. The coated electrode of claim 1, wherein the coating configured to improve electron transfer rate is made entirely or substantially of an inorganic conductive material.

14. The coated electrode of claim 13, wherein the inorganic conductive material comprises nanoparticles.

15. The coated electrode of claim 13, wherein the inorganic conductive material is selected from a group consisting of gold, platinum, and palladium.

16. The coated electrode of claim 13, wherein the coating configured to improve electron transfer rate is less than 100 nanometers.

17. The coated electrode of claim 1, wherein the coating configured to improve electron transfer rate is made entirely or substantially of graphene.

18. A biosensor comprising a plurality of electrodes, wherein:
   each of the plurality of electrodes comprises a coated electrode that includes:
      (a) an electrode;
      (b) a coating configured to immobilize biomolecules; and
      (c) a coating configured to improve electron transfer rate; and
   one or both of the following:
      (1) the coated electrode further comprises (d) a quinone that the electrode is configured to trigger to regulate or sense a pH level in a region local to the coated electrode; and
      (2) the coating configured to immobilize biomolecules comprises poly(ethylene glycol) carboxymethyl succinimidyl ester (PEG-NHS) polymers.

19. A method of modifying an electrode, the method comprising:
   (a) providing an electrode with a coating configured to immobilize biomolecules via one or more chemical groups; and
   (b) applying to the electrode a coating configured to improve electron transfer rate;
   wherein one or both of the following:
      (1) the method further comprises (c) applying to the electrode a quinone that the electrode is configured to trigger to regulate or sense a pH level in a region local to the electrode; and (2) the coating configured to immobilize biomolecules comprises poly(ethylene glycol) carboxymethyl succinimidyl ester (PEG-NHS) polymers.

20. The method of claim 19, wherein the coating configured to immobilize biomolecules comprises the poly(ethylene glycol) carboxymethyl succinimidyl ester (PEG-NHS) polymers.

21. The method of claim 19, wherein the electrode is an indium tin oxide electrode.

22. The method of claim 19, wherein the coating configured to improve electron transfer rate is made entirely or substantially of conductive organic polymers.

23. The method of claim 22, wherein the conductive organic polymers are selected from a group consisting of polyanilines, polythiophenes, polypyrroles, polyindoles, and polyphenylenes.

24. The method of claim 22, further comprising:
inactivating the one or more chemical groups of the coating configured to immobilize biomolecules prior to applying the coating configured to improve electron transfer rate; and
reactivating the one or more chemical groups subsequent to applying the coating configured to improve electron transfer rate.

25. The method of claim 24, wherein the one or more chemical groups are deactivated using hydrolysis.

26. The method of claim 22, wherein the coating configured to improve electron transfer rate is applied using electropolymerization.

27. The method of claim 19, wherein the coating configured to improve electron transfer rate is made entirely or substantially of an inorganic conductive material.

28. The method of claim 27, wherein the inorganic conductive material comprises nanoparticles.

29. The method of claim 27, wherein the inorganic conductive material is selected from a group consisting of gold, platinum, and palladium.

30. The method of claim 27, wherein the coating configured to improve electron transfer rate is applied using a technique selected from a group consisting of vapor-phase deposition, electroplating, electrodeposition, and solution-phase deposition.

31. The method of claim 27, wherein the coating configured to improve electron transfer rate is less than 100 nanometers.

32. The method of claim 19, wherein the coating configured to improve electron transfer rate is made entirely or substantially of graphene.

33. The method of claim 32, wherein the coating configured to improve electron transfer rate is applied using electrodeposition or covalent attachment.

34. A method of modifying an electrode, the method comprising:
(a) providing an electrode;
(b) applying to the electrode a coating configured to improve electron transfer rate;
(c) incorporating one or more chemical handles onto the coating configured to improve electron transfer rate; and
(d) applying to the electrode a coating configured to immobilize biomolecules via one or more chemical groups, wherein the one or more chemical handles are configured to bind the coating configured to immobilize biomolecules to the coating configured to improve electron transfer rate;
wherein one or both of the following:
(1) the method further comprises (c) applying to the electrode a quinone that the electrode is configured to trigger to regulate or sense a pH level in a region local to the electrode; and
(2) the coating configured to immobilize biomolecules comprises poly(ethylene glycol) carboxymethyl succinimidyl ester (PEG-NHS) polymers.

35. The method of claim 34, wherein the coating configured to immobilize biomolecules comprises the poly(ethylene glycol) carboxymethyl succinimidyl ester (PEG-NHS) polymer.

36. The method of claim 34, wherein the electrode is an indium tin oxide electrode.

37. The method of claim 34, wherein the one or more chemical handles is selected from a group consisting of carboxylates, amines, and thiols.

38. The method of claim 34, wherein the coating configured to improve electron transfer rate is made entirely or substantially of a conductive organic polymer.

39. The method of claim 38, wherein the conductive organic polymer is selected from a group consisting of polyanilines, polythiophenes, polypyrroles, polyindoles, and polyphenylenes.

40. The method of claim 38, wherein the coating configured to improve electron transfer rate is made entirely or substantially of an inorganic conductive material.

41. The method of claim 40, wherein the inorganic conductive material is platinum or palladium.

42. The method of claim 34, wherein the coating configured to improve electron transfer rate is made entirely or substantially of graphene.

43. A method comprising:
contacting a coated electrode with a solution that includes a quinone, wherein the coated electrode includes (a) an electrode, (b) a coating configured to immobilize biomolecules, and (c) a coating configured to improve electron transfer rate;
measuring a pH level of a region local to the coated electrode; and
adjusting the pH level;
wherein the measuring and adjusting of the pH level includes applying a charge to the coated electrode to activate the quinone.

* * * * *